(12) United States Patent
Choi et al.

(10) Patent No.: US 12,558,964 B2
(45) Date of Patent: Feb. 24, 2026

(54) VEHICLE PROVIDING NOTIFICATION INFORMATION FOR SAFETY OF A USER

(71) Applicants: Hyundai Motor Company, Seoul (KR); Kia Corporation, Seoul (KR)

(72) Inventors: JunHyuk Choi, Seoul (KR); CheolHan Kim, Gyeonggi-do (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 324 days.

(21) Appl. No.: 17/867,302

(22) Filed: Jul. 18, 2022

(65) Prior Publication Data

US 2023/0150369 A1     May 18, 2023

(30) Foreign Application Priority Data

Nov. 18, 2021     (KR) ........................ 10-2021-0159192

(51) Int. Cl.
| | |
|---|---|
| B60L 58/14 | (2019.01) |
| A61N 1/08 | (2006.01) |
| B60L 3/00 | (2019.01) |
| B60L 3/12 | (2006.01) |
| B62D 1/06 | (2006.01) |

(52) U.S. Cl.
CPC .................. B60L 3/12 (2013.01); A61N 1/08 (2013.01); B60L 3/0076 (2013.01); B60L 58/14 (2019.02); B62D 1/065 (2013.01)

(58) Field of Classification Search
None
See application file for complete search history.

(56) References Cited

U.S. PATENT DOCUMENTS

| | | | | |
|---|---|---|---|---|
| 8,188,868 | B2 * | 5/2012 | Case, Jr. .................. | A43B 3/34 36/137 |
| 10,403,113 | B1 * | 9/2019 | Antar ...................... | G01V 3/081 |
| 2006/0049943 | A1 * | 3/2006 | Sakashita ............... | G01V 15/00 340/572.1 |
| 2009/0224523 | A1 * | 9/2009 | Park ........................ | B62D 1/065 280/771 |
| 2011/0270362 | A1 * | 11/2011 | Goedeke .................. | A61N 1/05 607/116 |
| 2012/0001751 | A1 * | 1/2012 | Baker ................... | H04W 48/14 340/539.12 |
| 2015/0255994 | A1 * | 9/2015 | Kesler ................... | B60L 53/124 307/10.1 |
| 2016/0114687 | A1 * | 4/2016 | Ichikawa ................ | B60L 53/38 307/104 |
| 2017/0230743 | A1 * | 8/2017 | Lee ....................... | H04R 1/1041 |
| 2017/0315162 | A1 * | 11/2017 | Ambrosio ........... | H04M 19/047 |
| 2018/0034509 | A1 * | 2/2018 | Nakano ................... | H02J 50/60 |
| 2018/0164350 | A1 * | 6/2018 | Thompson ........... | G01R 29/085 |
| 2020/0021144 | A1 * | 1/2020 | Budhia .................. | H01F 27/36 |
| 2021/0226627 | A1 * | 7/2021 | Hirzmann ............... | B62D 1/06 |
| 2022/0185180 | A1 * | 6/2022 | Lin ....................... | B60W 40/08 |

* cited by examiner

*Primary Examiner* — Jason Holloway
*Assistant Examiner* — Bryant Tang
(74) *Attorney, Agent, or Firm* — Fox Rothschild LLP

(57) ABSTRACT

Provided is a vehicle that, in order to promote the safety of a user having an active implantable medical device implanted therein, is configured to acquire a strength of a magnetic field inside the vehicle, notify the user of the strength of the magnetic field, and control at least one electric device among a plurality of electric devices in the vehicle, in order to reduce the strength of the magnetic field. The vehicle may be a combustion engine vehicle and/or an electric vehicle.

20 Claims, 8 Drawing Sheets

1

<u>1</u>

<u>2</u>

VEHICLE PROVIDING NOTIFICATION INFORMATION FOR SAFETY OF A USER

CROSS-REFERENCE TO RELATED APPLICATION

This application claims, under 35 U.S.C. § 119(a), the benefit of Korean Patent Application No. 10-2021-0159192, filed on Nov. 18, 2021 in the Korean Intellectual Property Office, the disclosure of which is incorporated herein by reference in its entirety.

BACKGROUND

Technical Field

Embodiments of the present disclosure relate to a vehicle that is configured to output notification information for the safety of a user and/or is configured to control the operation of internal electric devices for the safety of a user.

Description of the Related Art

Many vehicles are internal combustion engine vehicles (e.g., general engine-driven vehicles) that are configured to generate mechanical power by, e.g., burning petroleum fuels, such as gasoline and light oil, and travel using mechanical power. Some vehicles are eco-friendly vehicles that are configured to travel, either entirely or partially, on electricity to enhance fuel efficiency and reduce toxic gas emissions.

Eco-friendly vehicles include, e.g.: electric vehicles that include a battery, which is a rechargeable power unit, and a motor such that the motor is rotated using the electricity accumulated in the battery and drives vehicle wheels using the rotation of the motor; hybrid vehicles that include an engine, a battery, and a motor, and travel by controlling the mechanical power of the engine and the electric power of the motor; and hydrogen fuel cell vehicles.

Vehicles may be equipped with various devices for occupant protection, traveling assistance, and improved riding comfort. Since the devices operate using electricity, most of the devices generate electromagnetic waves.

Vehicles may be configured to be used by users with active implantable medical devices, such as cardiac pacemakers, nerve stimulators, infusion pumps, circulatory support devices, cardiac defibrillators, and cochlear implants implanted into users, and electromagnetic waves generated by the devices of the vehicles may cause malfunctions of such active implantable medical devices. In this case, active implantable medical devices may threaten the health of the user.

Currently, since electronic devices provided in vehicles are diversifying, and the number of users with active implantable medical devices is increasing, there is a need for technologies of preventing electromagnetic waves generated from vehicles from adversely affecting active implantable medical devices of users.

SUMMARY

It is an object of the disclosure to provide a vehicle, in order to promote the safety of a user having an active implantable medical device implanted therein, capable of acquiring a strength of a magnetic field inside the vehicle, informing the user of the acquired strength of the magnetic field, and controlling an operation of at least one electric device among a plurality of electric devices inside the vehicle to reduce the strength of the magnetic field in the vehicle.

The technical objectives of the present disclosure are not limited to the above, and other objectives may become apparent to those of ordinary skill in the art based on the following descriptions.

According to an aspect of the present disclosure, there is provided a vehicle including: a display; a resistive wire provided on a steering wheel; a current sensor configured to detect an amount of current flowing through the resistive wire; and a processor configured to acquire a strength of a magnetic field generated in a vicinity of the steering wheel on a basis of the amount of current detected by the current sensor, and control the display to display notification information about a danger on the basis of the acquired strength of the magnetic field and a reference strength.

The display may be provided on at least one of a cluster or a terminal.

The reference strength may comprise a magnetic field strength corresponding to a standard magnetic field strength of an active implantable medical device.

The vehicle may further include a plurality of electric devices, wherein, when the acquired strength of the magnetic field is greater than or equal to the reference strength, the processor may be further configured to check a priority order of the plurality of electric devices, identify an electric device, of the plurality of electric devices, having a highest priority, and stop an operation of the identified electric device.

The vehicle may further comprise a plurality of electric devices, wherein, when the acquired strength of the magnetic field is greater than or equal to the reference strength, the processor may be further configured to check a priority order of the plurality of electric devices, identify an electric device having a highest priority, and change an operation level of the identified electric device.

The vehicle may further comprise a plurality of electric devices, wherein, when the acquired strength of the magnetic field is greater than or equal to the reference strength, the processor may be further configured to check amounts of current of the plurality of electric devices, identify an electric device having a largest amount of current on the basis of the checked amounts of current of the plurality of electric devices, and stop an operation of the identified electric device.

The vehicle may further include a plurality of electric devices, wherein, when the acquired strength of the magnetic field is greater than or equal to the reference strength, the processor may be further configured to check amounts of current of the plurality of electric devices, identify an electric device having a largest amount of current on a basis of the checked amounts of current of the plurality of electric devices priority, and change an operation level of the identified electric device.

The processor may be configured to check radius information of the steering wheel, position information of the steering wheel, position information of a seat, and angle information of a seat back of the seat, and acquire the strength of the magnetic field on a basis of the radius information of the steering wheel, the position information of the steering wheel, the position information of the seat, the angle information of the seat back of the seat, and the detected amount of current.

The processor may be configured to stop an operation of at least one of an conditioner, a resistive wire of a seat, and a heater when an outside temperature is higher than a first reference temperature and lower than a second reference temperature.

The processor may be configured to stop an operation of an amplifier of a sound outputter when the outside temperature is lower than or equal to the first reference temperature or higher than or equal to the second reference temperature.

According to another aspect of the disclosure, there is provided a vehicle including: a battery; a driving motor configured to generate a driving force using electric power charged in the battery, perform regenerative braking, and allow the battery to be charged through the regenerative braking; a display; a resistive wire provided on a steering wheel; a current sensor configured to detect an amount of current flowing through the resistive wire; and a processor configured to acquire a strength of a magnetic field generated in a vicinity of the steering wheel on a basis of the amount of current detected by the current sensor, control a display of notification information about a danger on the basis of the acquired strength of the magnetic field and a reference strength, and control regenerative braking of the driving motor.

The processor may be further configured to check a charge amount of the battery when the acquired strength of the magnetic field is greater than or equal to the reference strength, and, when the charge amount checked as being greater than or equal to a reference charge amount, stop the regenerative braking.

The reference strength may comprise a magnetic field strength corresponding to a standard magnetic field strength of an active implantable medical device.

The vehicle may further comprise a plurality of electric devices, wherein, when the acquired strength of the magnetic field is greater than or equal to the reference strength, the processor may be further configured to check a priority order of the plurality of electric devices, identify an electric device having a highest priority, and stop an operation of the identified electric device or change an operation level of the identified electric device.

The vehicle may further comprise a plurality of electric devices, wherein, when the acquired strength of the magnetic field is greater than or equal to the reference strength, the processor may be further configured to check amounts of current of the plurality of electric devices, identify an electric device having a largest amount of current on a basis of the checked amounts of current of the plurality of electric devices, and stop an operation of the identified electric device or change an operation level of the identified electric device.

The processor may be further configured to check radius information of the steering wheel, position information of the steering wheel, position information of a seat, and angle information of a seat back of the seat, and acquire the strength of the magnetic field on a basis of the radius information of the steering wheel, the position information of the steering wheel, the position information of the seat, the angle information of the seat back of the seat, and the detected amount of current.

The processor may be further configured to stop an operation of at least one of an air conditioner, a resistive wire of a seat, or a heater when an outside temperature is higher than a first reference temperature and lower than a second reference temperature.

The processor may be further configured to stop an operation of an amplifier of a sound outputter when the outside temperature is lower than or equal to the first reference temperature or higher than or equal to the second reference temperature.

The processor may be further configured to control the display to display the notification information when the acquired strength of the magnetic field is greater than or equal to the reference strength.

The current sensor may be further configured to detect an amount of current induced on the resistive wire when the resistive wire is in an off state.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
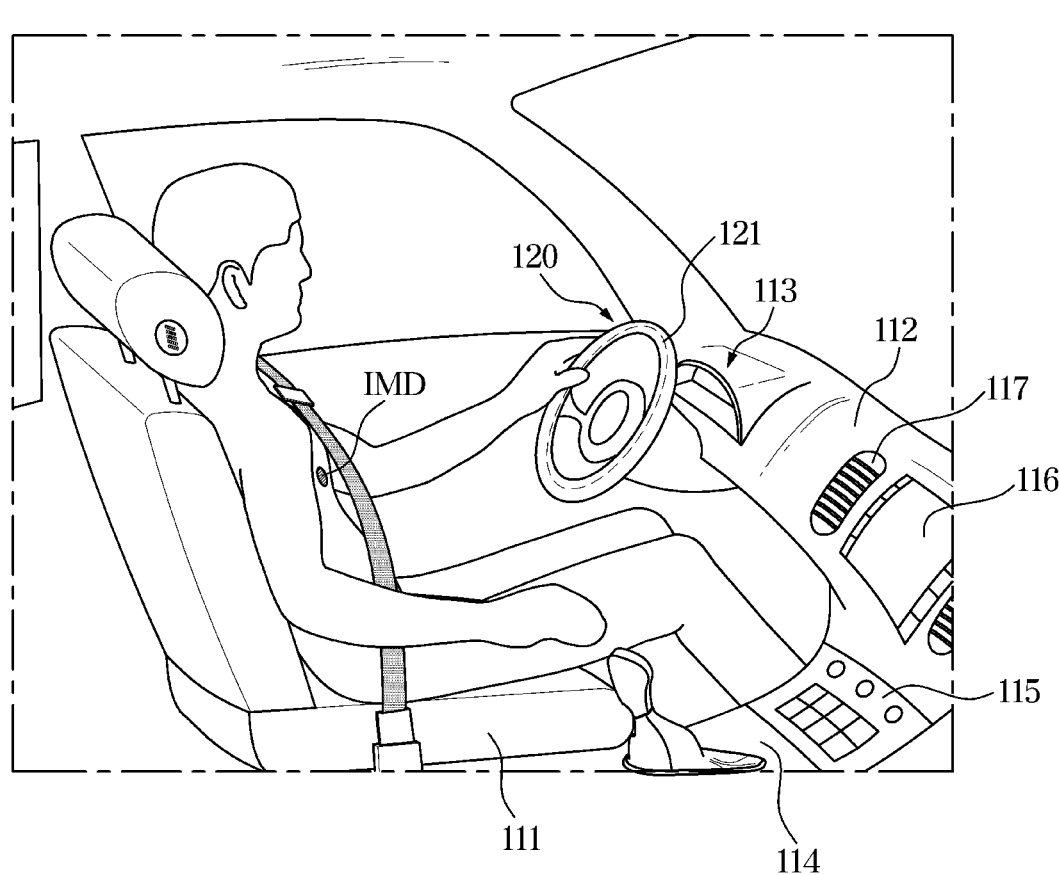
FIG. 1 is a diagram illustrating an interior of a vehicle according to an exemplary embodiment.

Like numerals refer to like elements throughout the specification. Not all elements of embodiments of the present disclosure will be described, and description of what are commonly known in the art or what overlap each other in the embodiments will be omitted. The terms as used throughout the specification, such as "~ part", "~ module", "~ member", "~ block", etc., may be implemented in software and/or hardware, and a plurality of "~ parts", "~ modules", "~ members", or "~ blocks" may be implemented in a single element, or a single "~ part", "~ module", "~ member", or "~ block" may include a plurality of elements.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. These terms are merely intended to distinguish one component from another component, and the terms do not limit the nature, sequence or order of the constituent components. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor and is specifically programmed to execute the processes described herein. The memory is configured to store the modules and the processor is specifically configured to execute said modules to perform one or more processes which are described further below.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about".

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless the context clearly indicates otherwise.

Although the terms "first," "second," "A," "B," etc. may be used to describe various components, the terms do not limit the corresponding components, but are used only for the purpose of distinguishing one component from another component.

Reference numerals used for method steps are just used for convenience of explanation, but not to limit an order of the steps. Thus, unless the context clearly dictates otherwise, the written order may be practiced otherwise.

Hereinafter, some embodiments of the present disclosure will be described in detail with reference to the exemplary drawings. In the drawings, the same reference numerals will be used throughout to designate the same or equivalent elements. In addition, a detailed description of well-known features or functions will be ruled out in order not to unnecessarily obscure the gist of the present disclosure.

FIG. 1 is a diagram illustrating an interior of a vehicle according to an exemplary embodiment, and the interior of the vehicle is described with reference to FIGS. 2 to 4.

Figure 2:
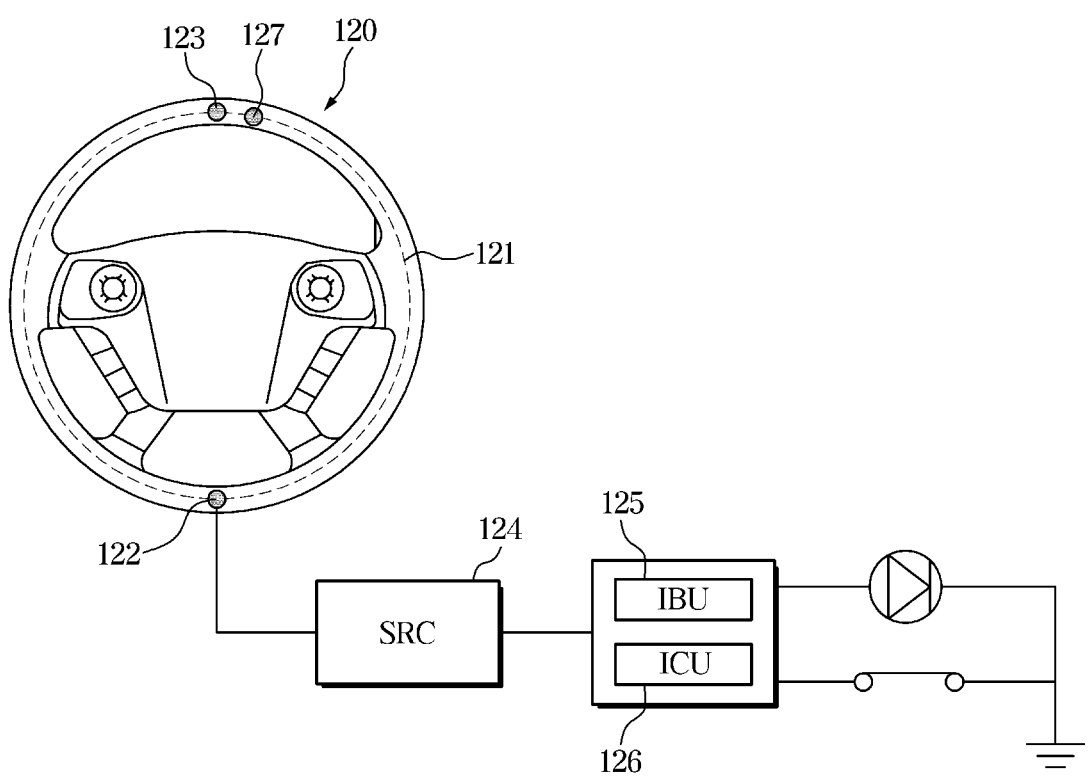
FIG. 2 is a diagram illustrating a steering wheel provided in a vehicle according to an exemplary embodiment.
Figure 3:
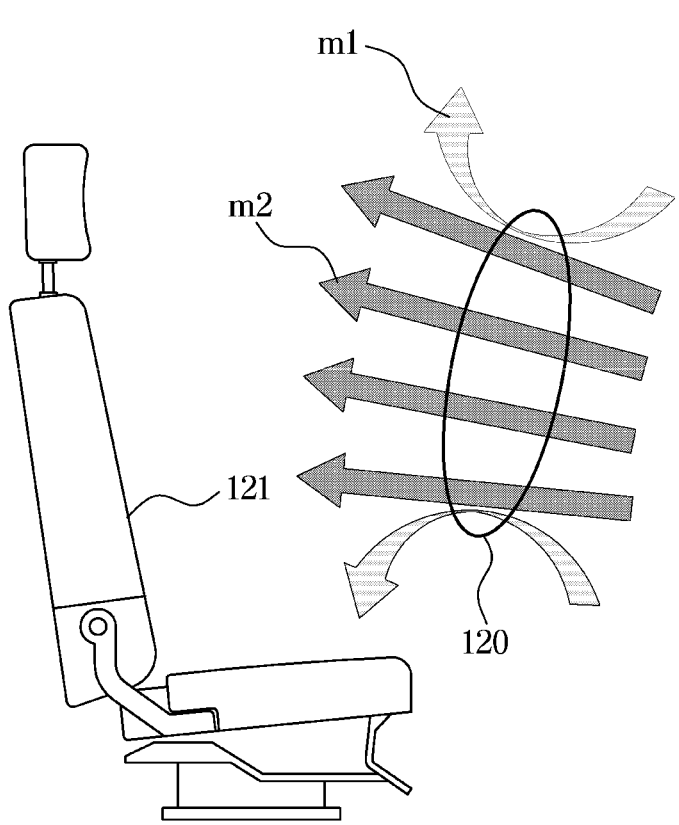
FIG. 3 is a diagram illustrating a magnetic field generated by a resistive wire of a steering wheel provided in a vehicle according to an exemplary embodiment.
Figure 4:
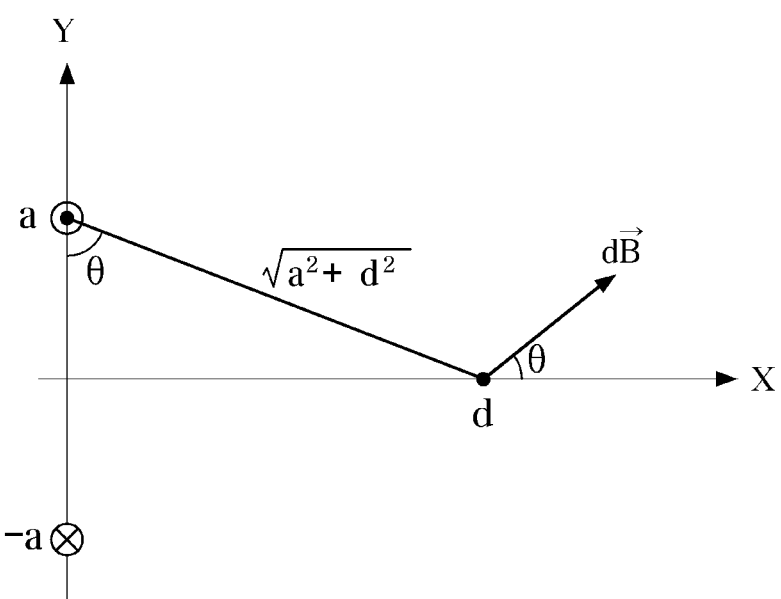
FIG. 4 is a diagram illustrating prediction of a magnetic field generated inside a vehicle according to an exemplary embodiment.

FIG. 2 is a diagram illustrating a steering wheel provided in a vehicle according to an exemplary embodiment, FIG. 3 is a diagram illustrating a magnetic field generated by a resistive wire of a steering wheel provided in a vehicle according to an exemplary embodiment, and FIG. 4 is a diagram illustrating prediction of a magnetic field generated inside a vehicle according to an exemplary embodiment.

A vehicle 1 includes a body having an interior and an exterior, and a chassis which is a part of the vehicle 1, except for the body, in which mechanical devices required for traveling are installed.

The exterior of the body may include a front panel, a bonnet, a roof panel, a rear panel, a tail gate, front and rear, left and right doors, and window glasses provided on the front and rear, left and right doors provided to be openable and closable.

Referring to FIG. 1, the interior of the body may include a seat 111 on which an occupant sits, a dashboard 112, an instrument board 113 (i.e., a cluster 113) disposed on the dashboard 112 and mounting a tachometer, a speedometer, a coolant thermometer, a fuel gauge, a turn indicator, a high-beam light, a warning light, a seat belt warning light, an odometer, an odograph, an automatic shift selector light, a door open warning light, an engine oil notification light, and a low fuel warning light thereon, a center fascia 114 in which a vent and a control panel of an air conditioner are disposed and an audio device is disposed, a head unit 115 provided on the center fascia 114 and controlling an audio device, an air conditioner, and a heater, a terminal (audio video navigation: AVN) configured to receive an operation command for at least one function among a plurality of functions, and configured to output operation information for the at least one function, and a vent 117 for blowing air having heat exchanged by the air conditioner to the inside of the vehicle using a fan.

The terminal 116 may be configured to display navigation information, music reproduction information, road information, and the like.

The seat 111 may be provided at an inside thereof with at least one of a ventilation device and a seat resistive wire, and the dashboard 112 may be provided at an inside thereof with a fan of the air conditioner.

The head unit 115 may be provided with an inputter for receiving an operation command of at least one function, and a display for displaying operation information of various functions and information input by the user.

The interior of the vehicle may be further provided with a global positioning system (GPS) receiver, a Bluetooth device, and a high-pass device installed for the convenience of the driver.

The chassis of the vehicle 1 may include a driving device, such as a power generating device, a power transmitting device, a steering device, a braking device, a suspension device, and a transmission device for applying a driving force and a braking force to the front, rear, left, and right vehicle wheels.

Here, based on the power generating device and the power transmitting device, vehicles 1 may be classified into an internal combustion engine vehicle or an eco-friendly vehicle.

In the case of an internal combustion engine vehicle, the power generating device may include an engine, a fuel device, a cooling and refueling device, and an electric device.

In the case of an electric vehicle among eco-friendly vehicles, the power generating device may include a battery and a driving motor.

In the case of a plug-in hybrid vehicle among eco-friendly vehicles, the power generating device may include a battery, a driving motor, an engine, a fuel device, and a cooling and refueling device.

The vehicle 1 may further include a start button for inputting an operation command to a starter motor (not shown). An internal combustion engine vehicle may be configured to, when the start button is turned on, operate a starter motor (not shown) and drive an engine (not shown), which is a power generating device, through the operation of the starter motor.

The chassis of the vehicle 1 may include a frame configured to support the body of the vehicle 1, and may include a plurality of vehicle wheels, a steering wheel 120 rotated by the user according to an intention of a user to steer, a brake pedal pressed by the user according to an intention of a user to brake, and an accelerator pedal pressed by the user according to an intention of a user to accelerate.

The brake pedal may be configured to receive a braking command corresponding to a pressing operation of a user, the accelerator pedal may be configured to receive an acceleration command corresponding to a pressing operation of a user, and the steering wheel 120 may be configured to receive a steering command corresponding to a rotational operation of a user.

The brake pedal, the accelerator pedal, and the steering wheel 120 may be provided inside the vehicle.

The steering wheel 120 may be provided with a resistive wire 121 for supplying heat to the steering wheel 120. The resistive wire 121 may be used as a device for predicting a magnetic field generated inside a vehicle.

Referring to FIG. 2, the steering wheel 120 may be further provided with a temperature sensor 122 for detecting the temperature of the resistive wire 121 or the temperature of the steering wheel 120, and a resistive wire controller 123 for controlling the resistive wire 121.

The temperature sensor 122 may include a resistor having a negative temperature coefficient in which the resistance value decreases when the temperature rises. The temperature sensor 122 may include a negative temperature coefficient-thermic resistor (NTC) thermistor.

The resistive wire controller 123 may be configured to adjust the amount of current flowing through the resistive wire 121 based on temperature information about the temperature detected by the temperature sensor 122 and target temperature information such that the temperature of the resistive wire 121 is maintained at the target temperature.

The steering wheel 120 may be connected to a steering roll connector 124, an integrated body control unit (IBU) 125 and an integrated central control unit (ICU) 126.

The steering roll connector 124 may serve to connect an electrical circuit to the steering wheel 120.

The steering roll connector 124 may be configured to transmit power or signals to an airbag module, a remote controller switch, or a horn provided adjacent to the steering wheel 120, even when the steering wheel 120 rotates.

The IBU 125 may be configured to perform smart key and door opening/closing control, and may be configured to monitor tire pressure and the like.

The IBU 125 may be configured to transmit an operation command to the resistive wire resistive wire controller 123 of the steering wheel 120.

The ICU 125 may be configured to convert the power of the battery provided in the vehicle to 5V dc, may be configured to control electrical output for electric devices provided in the vehicle, may be configured to maintain a constant voltage, and may be configured to perform input/output of CAN communication signals.

The ICU 125 may be configured to supply power to the resistive wire controller 123 of the steering wheel 120, the temperature sensor 122, and the resistive wire.

That is, the resistive wire controller 123 may be configured to perform an operation in response to a control command of the IBU 125 received through the steering roll connector 124, and may be supplied with power received from the ICU 125 through the steering roll connector 124.

The resistive wire controller 123 may be configured to predict a magnetic field generated inside the vehicle for the safety of a user into which an active implantable medical device (IMD or AIMD) is implanted.

The active implantable medical device may be a medical device that is fully or partially implanted into the human body and may be maintained in the implanted position for diagnostic or therapeutic purposes, and may be designed to be in direct contact with the human body for a long period of time. Accordingly, the active implantable medical devices may be required to conform strict standards (e.g., magnetic field strength and frequency, etc.) to protect the user's health and safety.

For example, the active implantable medical devices may include medical devices, such as, e.g., implantable cardiac pacemakers, implantable defibrillators, ventricular assist devices, brachytherapy systems, implantable infusion pumps, ventricular assist devices (VADs), cochlear implants, Implantable neuro-stimulator systems, implantable glucose monitors, Micro Electro-Mechanical Systems (MEMS), etc. The resistive wire 121 provided in the steering wheel 120 may be used as a loop antenna. Accordingly, not only an operating current for operating the resistive wire 121 but also an induced current induced by a magnetic field generated by various electric devices provided in the vehicle may flow through the resistive wire 121.

The various electric devices provided in the vehicle may also include a user terminal (not shown).

The user terminal may be implemented as a computer or a portable terminal capable of connecting to the vehicle through a network. Here, the computer may include, for example, a notebook computer, a desktop computer, a laptop PC, a tablet PC, a slate PC, and the like, each of which may be equipped with a WEB Browser. The portable terminal may be a wireless communication device with a portability and mobility, for example: all types of handheld based wireless communication devices, such as a personal communication system (PCS), a global system for mobile communications (GSM), a personal digital cellular (PDC), a personal handyphone system (PHS), a personal digital assistant (PDA), an international mobile telecommunication (IMT)-2000, a code division multiple access (CDMA)-2000, a W-code division multiple access (W-CDMA), a wireless broadband internet (WiBro) terminal, a smart Phone, and the like; and wearable devices, such as a watch, a ring, a bracelet, an ankle bracelet, a necklace, glasses, a contact lens, or a head-mounted-device (HMD).

The user terminal may be configured to, upon determining that the strength of the magnetic field reaching the driver is greater than or equal to a reference strength, display notification information about a danger, and display information about devices of which operating states have been changed among a plurality of electric devices in the vehicle 1.

The resistive wire controller 123 may be configured to monitor the magnetic field generated in the vicinity of the center of the steering wheel 120 by checking the amount of a target current for the operation of the resistive wire 121, checking the amount of an induced current induced in the resistive wire 121, summing the amount of the target current and the amount of the induced current, and acquiring the strength of the magnetic field generated in the vicinity of the center of the steering wheel 120 inside the vehicle based on the total amount of summed currents.

The resistive wire controller 123 may also be configured to acquire the amount of induced current flowing in the resistive wire based on the amount of current detected by an induction current sensor (not shown).

The resistive wire controller 123 may also be configured to acquire the total amount of current flowing through the resistive wire 121 based on current information detected by a current sensor 127 provided on the resistive wire 121.

The resistive wire controller 123 may be configured to acquire the total amount of current flowing in the resistive wire 121 based on current information detected by the current sensor 127 provided in the resistive wire 121, and may be configured to acquire the amount of induced current based on the acquired total amount of current and a target amount of current applied to the resistive wire 121.

Referring to FIG. 3, in the vicinity of the center of the steering wheel 120, a first magnetic field, m1, corresponding to the amount of the target current for the operation of the resistive wire 121, and a second magnetic field, m2, corresponding to the amount of induced current induced in the resistive wire 121 may be generated.

That is, the resistive wire controller 123 may be configured to acquire the magnetic field strength based on the first and second magnetic fields generated in the vicinity of the center of the steering wheel 120.

The resistive wire controller 123 may be configured to acquire the strength of the magnetic field generated at a point of the upper body of the driver based on the strength of the magnetic field generated in the vicinity of the center of the steering wheel 120.

The resistive wire resistive wire controller 123 may be configured to check radius information of the steering wheel, position information of the steering wheel, position information of a seat, and angle information of a seat back of the seat, and acquire a distance d' between the center position of the steering wheel and the center position of the seat based on the checked position information of the steering wheel, the checked position information of the seat, and the checked angle information of the seat back.

The resistive wire controller 123 may be configured to acquire a distance, d, from the center position of the steering wheel to the upper body of the driver based on an acquired distance, d', and the average chest thickness of adults.

The resistive wire controller 123 may be configured to acquire the distance, d, from the center position of the steering wheel to the upper body of the driver by subtracting a half of the average chest thickness of adults from the distance, d', between the center position of the steering wheel and the center position of the seat.

$$d = d' - 01 \cdot m$$

Here, the chest thickness of adults may be predetermined information, which is information acquired by experiments. For example, the average chest thickness of adult males is 209 mm, and the average chest thickness of adult females is 191 mm. That is, the average chest thickness of adults is about 200 mm.

Referring to FIG. 4, the magnetic fields in the Y-axis direction at a point corresponding to the distance d from the center position of the steering wheel to the center position of the driver's upper body may cancel each other to become 0, and only the magnetic fields in the X-axis direction may remain.

The resistive wire controller 123 may configured to, under the conditions of a radius 'a' of the steering wheel and the distance, d, from the center position of the steering wheel to the center position of the driver's upper body, acquire the strength of the magnetic field generated by the resistive wire 121 having a radius 'a', at a point corresponding to the distance, d, from the center position of the steering wheel to the center position of the driver's upper body.

That is, the resistive wire controller 123 may be configured to acquire the magnetic field, Bx, of the x-axis using the Biot-Savar law (formula).

$$\vec{B} = \frac{\mu_0}{4\pi} \int \frac{I \vec{dl} \times \hat{r}}{\gamma^2}$$

$$dB = \frac{\mu_0}{4\pi} \frac{Idl}{a^2 + d^2}$$

$$\cos \theta = \frac{a}{\sqrt{a^2 + d^2}}$$

$$\oint dl = 2\pi a$$

$$dB_x = dB \cos \theta = \frac{\mu_0}{4\pi} \frac{Idl}{a^2 + d^2} \frac{a}{\sqrt{a^2 + d^2}}$$

$$B_x = \frac{\mu_0 Ia}{4\pi} \int \frac{dl}{(a^2 + d^2)^{3/2}} = \frac{\mu_0 I}{2} \frac{a^2}{(a^2 + d^2)^{3/2}}$$

Here, $\mu_0$ is the permeability of the air, and 'I' is the total current flowing through the resistive wire of the steering wheel.

The resistive wire controller 123 may be configured to transmit information about the acquired strength of the magnetic field, Bx, of the x-axis to a processor 150 of the vehicle.

The acquired strength of the magnetic field, Bx, of the x-axis may be the strength of the magnetic field generated in the vicinity of the center of the steering wheel 120.

When the resistive wire 121 is in an off state, the resistive wire controller 123 may also be configured to acquire the strength of a magnetic field in the vicinity of the user's upper body based on the amount of the induced current induced in the resistive wire 121.

Figure 5:
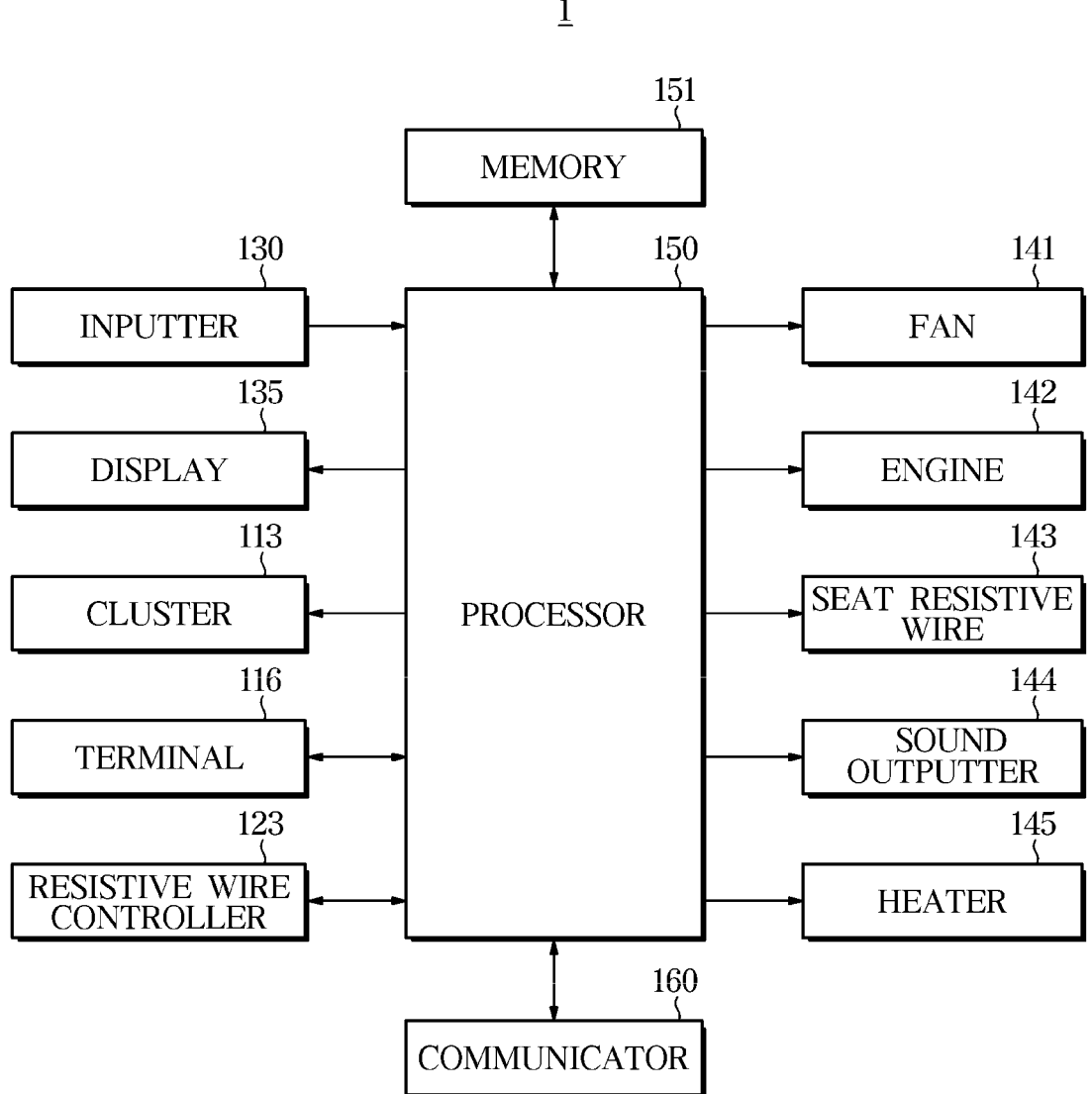
FIG. 5 is a control block diagram of a vehicle according to an exemplary embodiment.

FIG. 5 is a control block diagram of a vehicle according to an exemplary embodiment.

The vehicle 1 may include the cluster 113, the terminal 116, the inputter 130, a display 135, the fan 141, an engine 142, a seat resistive wire 143, a sound outputter 144, a heater 145, a processor 150, a memory 151, and a communicator 160.

The cluster 113 may be configured to display traveling information of the vehicle using power supplied from the vehicle 1, and may be configured to display notification information for user recognition.

The cluster 113 may include a display.

The cluster 113 may be configured to display notification information for the user safety through the display in response to a control command of the processor 150.

The terminal 116 may be configured to display various types of information about functions performed in the vehicle using the power supplied from the vehicle 1. The terminal 116 may be configured to display information about at least one of audio, video, and navigation functions, and may be configured to display a rear view image acquired by a camera (not shown). The terminal 116 may also a user input.

The inputter 130 may be provided in at least one of the head unit 115, the steering wheel 120, or the center fascia 114, and receive a user input.

The inputter 130 may be configured to receive on/off commands for at least one function among a plurality of functions, and may be configured to receive an operation command for the input at least one function.

The inputter 130 may also be configured to receive an on-command or an off-command of a safe mode for the user safety.

The inputter 130 may be configured to receive identification information of the active implantable medical device.

The inputter 130 may be configured to receive standard magnetic field information and standard frequency information of the active implantable medical device.

The display 135 may be configured to display operation information about a function being performed in the vehicle.

The display 135 may be configured to display on-information and off-information of the safe mode.

The display 135 may be configured to display notification information for user safety in response to a control command of the processor 150. As an example, the display 135 may be configured to display a reference strength corresponding to the standard magnetic field strength of the active implantable medical device and the strength of a magnetic field generated inside the vehicle, and may be configured to display operation control information about at least one electric device for reducing the strength of the magnetic field generated inside the vehicle.

The fan 141 may be configured to rotate in response to the operation of the air conditioner so that the air having heat exchanged by the air conditioner is blown into the interior of the vehicle.

The engine 142, as a power device of the vehicle, may be configured to generate a driving force of the vehicle.

The seat resistive wire 143 may be provided in the seat 111, may be configured to perform on or off operation in response to a control command of the processor 150, and may be configured to apply heat to the seat 111 in an on-operation.

The sound outputter 144 may be configured to output a sound in response to a control command of the processor 150.

The sound outputter 144 may be provided in at least one of the interior or exterior of the vehicle.

The sound outputter 144 may include one or more speakers.

The speaker may be configured to generate a sound by converting a sound source into an electrical signal, amplifying the converted electrical signal, and converting the amplified electrical signal into vibration. Such a speaker may include an amplifier for amplifying an electrical signal.

As for the principle of the speaker, when a magnetic field is generated by a magnet provided in the speaker, a signal transmitted from the amplifier may be connected to a speaker terminal, and then current may be made to flow through the amplifier, so that a cone moves up and down to produce sound. In this case, when current flows from the amplifier, the speaker cone may move forward and backward, and the air density may change according to the cone movement, which may be detected by the user's ear, and recognized as sound.

The heater 145 is an electric device for increasing the temperature of the air inside the vehicle. The heater 145 may be turned on or off in response to a user input, and a target indoor temperature may be selected in response to the user input.

The heater 145 may be configured to generate heat in response to a control command of the processor 150.

The processor 150 may be configured to receive information about the standard magnetic field and standard frequency corresponding to the identification information of the active implantable medical device received by the inputter 130 through the communicator 160. That is, the processor 150 may be configured to receive the information about the standard magnetic field and standard frequency of the active implantable medical device from the server (not shown).

The processor 150 may be configured to check position information of the steering wheel, position information of the seat, and angle information of the seat back, and transmits the position information of the steering wheel, the position information of the seat, and the angle information of the seat back to the resistive wire controller 123, and transmits pre-stored radius information of the steering wheel to the resistive wire controller 123.

The processor 150 may be configured to, in response to a request of the resistive wire controller 123, transmit the position information of the steering wheel, the position information of the seat, the angle information of the seat back, and the radius information of the steering wheel to the resistive wire controller 123, or, in response to a setting value being changed by a user input, transmit the position information of the steering wheel, the position information of the seat, and the angle information of the seat back to the resistive wire controller 123.

The processor 150 may be configured to control the display 135 or the cluster 113 to display the strength of the magnetic field generated in the vicinity of the center of the steering wheel 120 or the upper body of the driver, which is a strength transmitted to the resistive wire controller 123. With such a configuration, the driver may identify the strength of the magnetic field reaching himself/herself in real time. The processor 150 may be configured to, upon determining that the strength of the magnetic field reaching the driver is greater than or equal to the reference strength, control the display 135 or the cluster 113 to display notification information about a danger. Here, the reference strength may be a strength corresponding to the standard magnetic field strength of the active implantable medical device.

The processor 150 may be configured to, upon determining that the strength of the magnetic field reaching the driver is greater than or equal to the reference strength, stop the operation of at least one electric device among a plurality of electric devices provided in the vehicle or change the operation level of the at least one electric device.

More specifically, the processor 150 may be configured to, upon determining that the acquired strength of the magnetic field is greater than or equal to the reference strength, check the priority order of the plurality of electric devices, identify an electric device having the highest priority, and stop the operation of the identified electric device, or change the operation level of the identified electric device.

The processor 150 may be configured to, upon determining that the acquired strength of the magnetic field is greater than or equal to the reference strength, check the priority order of the plurality of electric devices, identify a first electric device having the highest priority, and control stop the operation of the identified first electric device, and then may acquire the strength of the magnetic field again, and, upon determining that the acquired strength of the magnetic field is greater than or equal to the reference strength, identify a second electric device having the highest priority and control stop the operation of the identified second electric device.

In other words, the processor 150 may be configured to control stop the operation of the electric devices based on the priority order of the plurality of electric devices until the strength of the magnetic field becomes less than the reference strength.

The processor 150 may be configured to, upon determining that the acquired strength of the magnetic field is greater than or equal to the reference strength, check the priority order of the plurality of electric devices, change an operation level of a first electric device having the highest priority, and then acquire the strength of the magnetic field again, and, upon determining that the acquired strength of the magnetic field is greater than or equal to the reference strength, change an operation level of a second electric device having the highest priority.

In other words, the processor 150 may be configured to change the operation level of the electric devices based on the priority order of the plurality of electric devices until the strength of the magnetic field becomes less than the reference strength.

The priority order of the plurality of electric devices may be determined according to the amount of current or the use.

The processor 150 may be configured to check the degree of relevance to traveling based on the uses of the plurality of electric devices, and may be configured to set a higher priority order to an electric device checked as having a lower relevance to traveling.

The processor 150 may be configured to check the amounts of current of the plurality of electric devices, identify a first electric device checked as having the greatest amount of current, and control stop the operation of the identified first electric device, and then acquire the strength of the magnetic field again, and, upon determining that the acquired strength of the magnetic field is greater than or equal to the reference strength, identify a second electric device checked as having the second greatest amount of current and control stop the operation of the identified second electric device.

As an example, the processor 150 may be configured to, upon determining that the strength of the magnetic field is equal to or greater than the reference strength, turn off the amplifier of the sound outputter having a large amount of current.

In other words, the processor 150 may be configured to control stop the operation of the electric device based on the amount of current until the acquired strength of the magnetic field becomes less than the reference strength.

The processor 150 may be configured to check the amounts of current of the plurality of electric devices, identify a first electric device checked as having the greatest amount of current, change the operation level of the identified first electric device, and then acquire the strength of the magnetic field again, and, upon determining that the acquired strength of the magnetic field is greater than or equal to the reference strength, identify a second electric device checked as having the second greatest amount of current and change the operation level of the identified second electric device.

In other words, the processor 150 may be configured to change the operation level of the electric device based on the amounts of current until the acquired strength of the magnetic field becomes less than the reference strength.

In this case, the operation level of the electric devices may be changed by one level at a time according to the priority.

The processor 150 may be configured to, upon determining that the acquired strength of the magnetic field is greater than or equal to the reference strength, turn off the operation of at least one of the air conditioner, the seat resistive wire, or the heater based on the outdoor temperature acquired through an outdoor temperature sensor (not shown), or change the operation level of the at least one of the air conditioner, the seat resistive wire, or the heater.

The processor 150 may be configured to, upon determining that the outdoor temperature is higher than a first reference temperature and lower than a second reference temperature, change the operation level of at least one of the air conditioner, the seat heating element, or the heater.

The processor 150 may be configured to, upon determining that the state of charge (SOC) of the battery 201 is less than a reference SOC, check the outdoor temperature detected by the outdoor temperature sensor, and, upon determining that the outdoor temperature is higher than the first reference temperature and lower than the second reference temperature, identify an electric device in operation among the air conditioner, the seat resistive wire, and the heater, and, upon identifying that two or more electric devices are in operation, control stop at least one of the two or more electric devices.

The processor 150 may be configured to, upon determining that the outdoor temperature is lower than or equal to the first reference temperature or is higher than or equal to the second reference temperature, check a plurality of electric devices operating in the vehicle, and identify an electric device having the largest amount of current among the checked electric devices, and control stop the operation of the electric device having the largest amount of current.

The processor 150 may be configured to, after turning off the operation of at least one electric device, acquire the strength of the magnetic field periodically or in real time, and, when the acquired strength of the magnetic field becomes less than the reference strength, turn on the operation of the electric device that is turned off.

The processor 150 may be configured to, after changing the operation level of at least one electric device, acquire the strength of the magnetic field periodically or in real time, and, when the acquired strength of the magnetic field becomes less than the reference strength, resume the operation level before the change of the operation level of the electric device.

The processor 150 may be configured to check the difference value between the checked strength of the magnetic field and the reference strength, recognize at least one electric device for which the operation level needs to be changed based on the checked difference value, and change the operation level of the recognized at least one electric device.

The processor 150 may be configured to check the difference value between the checked strength of the magnetic field and the reference strength, and check the number of changes in which the operation level of at least one electric device is changed based on the checked difference value, and change the operation level of the electric device.

In this case, the operation level of one electric device may be changed by one level, two levels, or three levels at a time according to the difference value.

Information about the amount of change in the magnetic field strength corresponding to the amount of change in the operation level for each electric device may be stored in advance.

For example, the air conditioner may have a higher operation level as the target air conditioning temperature is lower. The sound outputter may have a higher operation level as the volume is higher.

The processor 150 may be configured to receive information about the total amount of current flowing through the resistive wire from the resistive wire controller 123, and, based on the received total amount of current, position information of the steering wheel, position information of the seat, angle information of the seat back, and radius information of the steering wheel, acquire information about the strength of the magnetic field that affects the driver.

The processor 150 may include a memory (not shown) configured for storing data regarding an algorithm for controlling the operations of the components of the vehicle 1 or a program that represents the algorithm, and a processor (not shown) that performs the above described operations using the data stored in the memory. In this case, the memory and the processor may be implemented as separate chips. Alternatively, the memory and the processor may be implemented as a single chip.

The memory 151 may be configured to store standard information of the active implantable medical device. The standard information of the active implantable medical device may include the reference strength corresponding to the standard magnetic field strength.

The memory 151 may be configured to store information about the first reference temperature and the second reference temperature for performing the safe mode.

The memory 151 may be configured to store information about the priority order of the plurality of electric devices.

The priority may be determined according to the amount of current flowing during operation. That is, as the amount of current flowing during operation is higher, a higher priority may be assigned.

The priority may be determined by a degree of relevance to the traveling of the vehicle. For example, a terminal performing a navigation function may have a degree of relevance higher than that of a seat resistive wire. That is, the priority of the seat resistive wire may be higher than that of the terminal.

The memory 151 may be configured to store information about the amount of current of each of the plurality of electric devices.

The memory 151 may be configured to store a plurality of operation levels for each of the electric devices.

For example, the air conditioner may have a plurality of operation levels respectively corresponding to a plurality of target air conditioning temperatures. The sound outputter may have a plurality of operation levels respectively corresponding to a plurality of volumes.

The memory 151 may include a nonvolatile memory device, such as a cache, a read only memory (ROM), a programmable ROM (PROM), an erasable programmable ROM (EPROM), an electrically erasable programmable ROM (EEPROM), and a flash memory, a volatile memory device, such as a random access memory (RAM), or other storage media, such as a hard disk drive (HDD), a CD-ROM, and the like, but the implementation of the memory 151 is not limited thereto.

The communicator 160 may be configured to perform communication between the processor 150 and the resistive wire controller 123.

The communicator 160 may include one or more components that enable communication with the processor 150 and the resistive wire controller 123, for example, at least one of a short-range communication module, a wired communication module, and a wireless communication module.

The short-range communication module may include various short-range communication modules that may transmit and receive signals in a short distance using a wireless communication network, for example, a Bluetooth module, an infrared communication module, a radio frequency identification (RFID) communication module, a wireless local access network (WLAN) communication module, a near field communication (NFC) communication module, a Zigbee communication module, and the like.

The wired communication module may include not only various wired communication modules, such as a controller area network (CAN) communication module, a local area network (LAN) communication module, a wide area network (WAN) module, or a value added network (VAN) module, but also various cable communication modules, such as a universal serial bus (USB), a high definition multimedia interface (HDMI), a digital visual interface (DVI), a recommended standard 232 (RS-232), power line communication, or plain old telephone service (POTS).

The wireless communication module may include various wireless communication modules for supporting various wireless communication methods, such as a Wifi module, a wireless broadband (Wibro) module, a global system for mobile communication (GSM), a code division multiple access (CDMA), a wideband code division multiple access (WCDMA), universal mobile telecommunications system (UMTS), a time division multiple access (TDMA), a long term evolution (LTE), and the like.

At least one component may be added or omitted to correspond to the performance of the components of the vehicle shown in FIG. 5. In addition, the mutual positions of the components may be changed to correspond to the performance or structure of the system.

The components shown in FIG. 5 may refer to a software component and/or a hardware component, such as a Field Programmable Gate Array (FPGA) and an Application Specific Integrated Circuit (ASIC).

Figure 6:
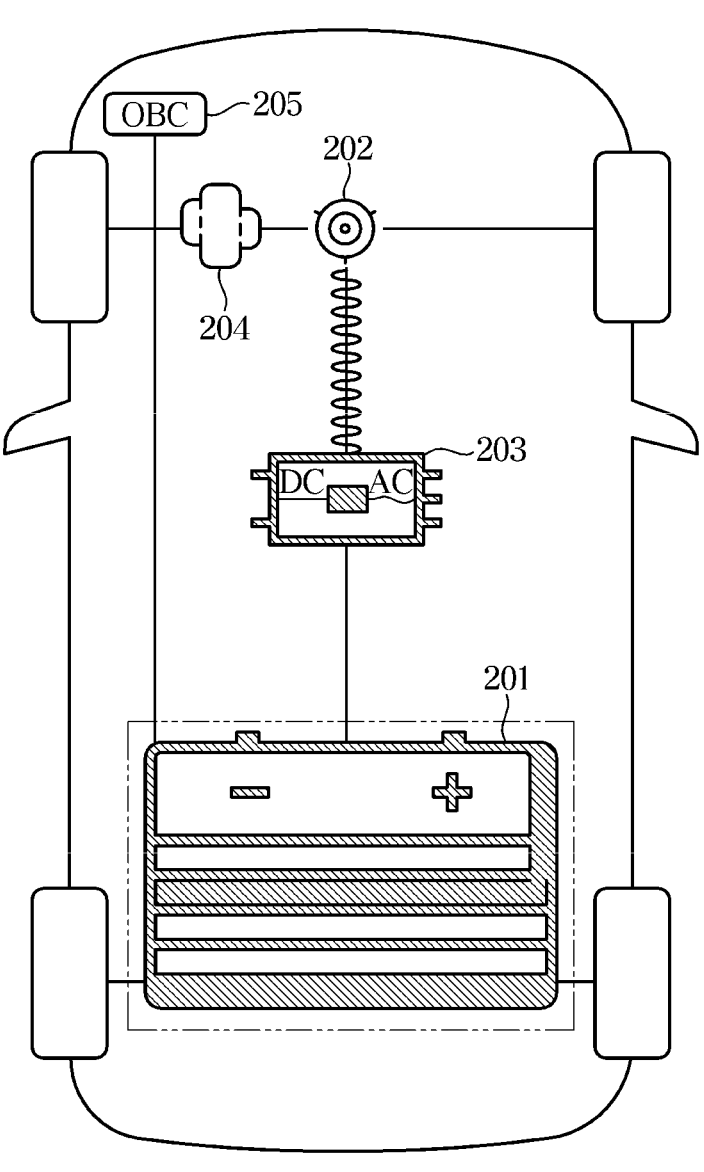
FIG. 6 is a diagram illustrating a power device of a vehicle according to another exemplary embodiment.

FIG. 6 is a diagram illustrating a power device of a vehicle according to another exemplary embodiment.

A vehicle 2 according to the embodiment may be an eco-friendly vehicle that travels using a battery and a motor, and may include an electric vehicle or a plug-in hybrid electric vehicle (PHEV). In the embodiment, an electric vehicle will be described as an example.

Referring to FIG. 6, the power device of the vehicle 2 may include a battery 201, a driving motor 202, a motor driver 203, a reducer 204, and a power converter 205.

The battery 201 may include a plurality of battery cells that may be configured to generate a high-voltage current to supply driving power to the vehicle 2.

The battery 201 may include a plurality of battery modules, and each of the battery modules may include a plurality of battery cells connected in series and in parallel.

The battery cells may form a battery module together with each other, and battery modules may form a battery pack together with each other.

The driving motor 202 may be configured to generate a rotational force using the electrical energy of the battery 201 and transmits the generated rotational force to the vehicle wheels to drive the vehicle wheels.

The driving motor 202 may be configured to convert electrical energy of the battery 201 into mechanical energy for operating various devices provided in the vehicle 2.

When a booting button is turned on, the driving motor 202 may be supplied with a maximum current to generate a maximum torque.

The driving motor 202 may be operated as a generator under energy regeneration conditions by braking, deceleration, downhill traveling, or low-speed traveling so that the battery 201 is charged. The driving motor 202 may be configured to perform regenerative braking and allows the battery to be charged through regenerative braking.

The motor driver 203 may be configured to drive the driving motor 202 in response to a control command of a first processor. The motor driver 203 may include an inverter (not shown) that converts power of a battery into driving power of the driving motor 202.

The inverter may be configured to, during output of driving power of the driving motor 202, output driving power of the driving motor 202 based on a target vehicle speed according to a user command. Here, the driving power of the driving motor 202 may vary according to a switching signal for outputting a current corresponding to the target vehicle speed and a switching signal for outputting a voltage corresponding to the target vehicle speed.

The inverter may also be configured to transfer power generated from the driving motor 202 to the battery 201 during regenerative braking. That is, the inverter may include a plurality of switch elements, and may be configured to perform a function of changing the direction and output of the current between the driving motor 202 and the battery 201.

The reducer 204 may be configured to transmit, to the vehicle wheels, a rotational force obtained by decelerating the speed of the driving motor 202 and increasing the torque of the driving motor 202.

The vehicle may further include a charger provided on the exterior of the body, connected with a fast charging cable or a slow charging cable, and may be configured to receive power for charging the battery 201.

The charger may include a fast charger, A1, for quickly charging the battery 201 and a slow charger, A2, for charging the battery 201 at a rate that is slower than that of the fast charging speed.

The vehicle 2 may further include a power converter (On Board Charge: OBC) 205 that may be configured to convert external commercial power (AC power) into rectified and direct current that is then transmitted to the battery 201. For example, the power converter 205 may include an AC rectifier, a power factor correction (PFC), a converter, and a capacitor.

Figure 7:
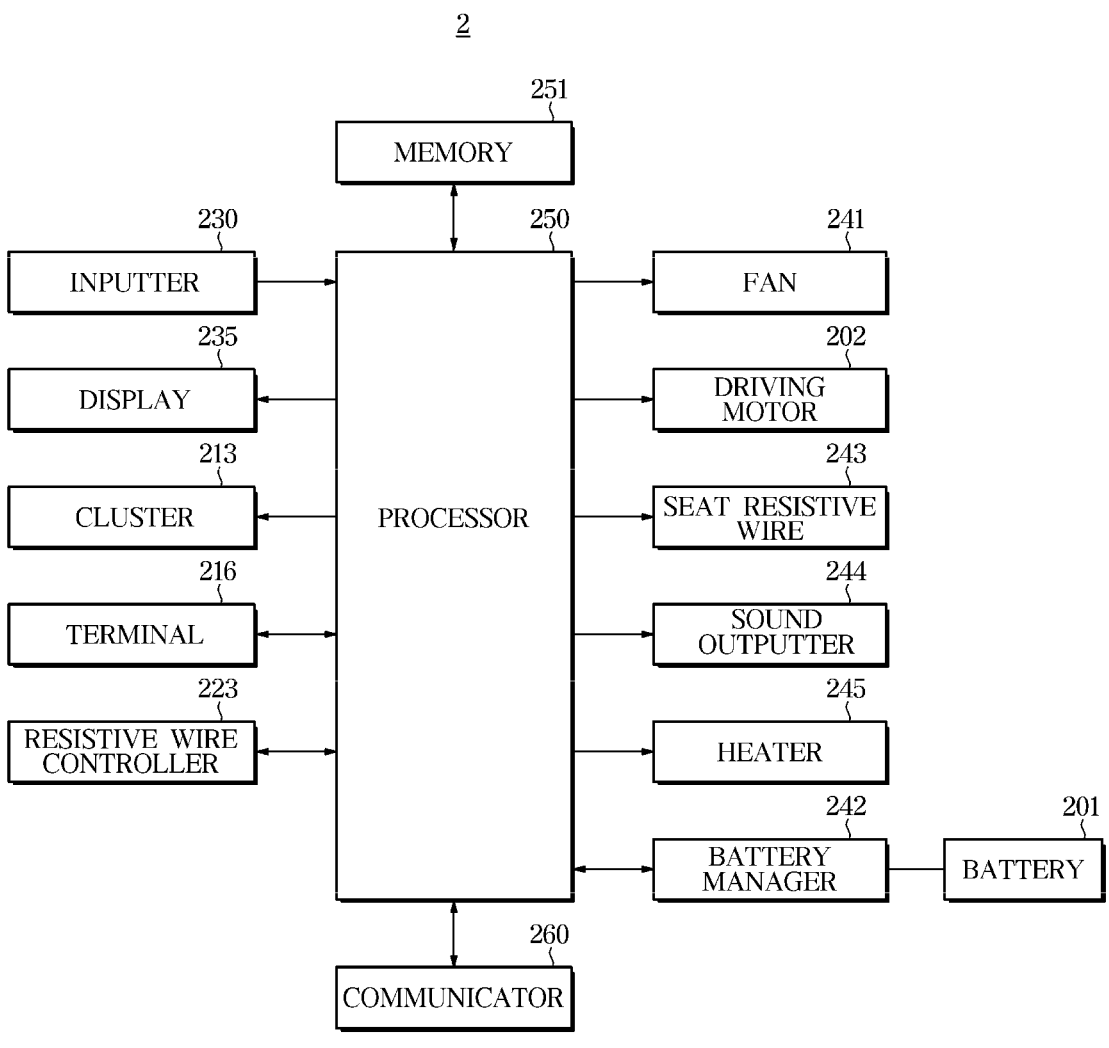
FIG. 7 is a control block diagram of a vehicle according to another exemplary embodiment.

FIG. 7 is a control block diagram of a vehicle according to another exemplary embodiment.

The vehicle 2 may include a battery 201, a driving motor 202, a cluster 213, a terminal 216, an inputter 230, a display 235, a fan 241, a battery manager 242, and a seat resistive wire 243, a sound outputter 244, a heater 245, a processor 250, a memory 251, and a communicator 260.

In the following description of the cluster 213, the terminal 216, the inputter 230, the display 235, the fan 241, the seat resistive wire 243, the sound outputter 244, the heater 245, and the communicator 260 provided in the vehicle 2 according to the embodiment, details of constructions identical to those of the cluster 113, the terminal 116, the inputter 130, the display 135, the fan 141, the seat resistive wire 143, the sound outputter 144, the heater 145, and the communicator 160 provided in the vehicle 1 according to the previous exemplary embodiment will be omitted.

The steering wheel, the resistive wire, the resistive wire controller, the temperature sensor, and the current sensor provided in the vehicle, according to the exemplary embodiment, are the same as the steering wheel, the resistive wire, the resistive wire controller, the temperature sensor, and the current sensor provided in the vehicle according to the above embodiment, and thus details thereof will be omitted in the following description.

The display 235 may also be configured to display SOC information of the battery 201.

The display 235 may be configured to display regenerative braking information about stopping regenerative braking or maintaining regenerative braking.

The SOC information of the battery 201 may include a charge amount of the battery and a charge level corresponding to the charge amount of the battery, and may include a reference charge amount. Here, the reference charge amount may be approximately a SOC of 10%.

The battery 201 may be a battery that is chargeable and dischargeable.

The battery 201 may be configured to supply driving power to power device s including the driving motor 202. The battery 201 may be configured to supply power to electronic devices, such as convenience devices and additional devices.

The battery manager 242 may be configured to monitor a state of charge, a state of discharge, and a state of failure of the battery 201.

The battery manager 110 may be configured to monitor the state of each battery cell in units of battery cells, may be configured to monitor the state of each battery module in units of battery modules, and may be configured to monitor the state of the battery pack.

The battery manager 242 may include a voltage detector, a current detector, and a temperature detector as detectors that detect the SOC of the battery in order to monitor the state of the battery 201.

The voltage detector may be configured to detect a voltage of the battery and output a voltage signal corresponding to the detected voltage. The voltage detector may be provided in plural.

The current detector may be configured to detect a current of the battery and output a current signal corresponding to the detected current. The current detector may be provided in plural.

The temperature detector may be configured to detect the temperature of the battery and output a temperature signal corresponding to the detected temperature. The temperature detector may be provided inside the battery pack. The temperature detector may be provided in plural.

The battery manager 242 may be configured to monitor the SOC of the battery 201 based on the detected current of the battery 201.

The battery manager 242 may be configured to monitor the SOC of the battery 201 based on the detected current and voltage of the battery.

The battery manager 242 may be configured to monitor the SOC of the battery based on the current, voltage, and temperature of each of the cells of the battery.

The battery manager 242 may be configured to acquire the SOC of the battery corresponding to the current, voltage, and temperature of the battery from a table stored in advance. In the pre-stored table, the charge amount of the battery may be matched according to a correlation with the current, voltage, and temperature of the battery 100.

The battery manager 242 may be configured to, upon receiving a boot-on command from the processor 250, check the SOC of the battery and transmit SOC information of the checked SOC of the battery to the processor 242.

The processor 250 may be configured to control the operation of the display 235 so that the SOC information of the battery transmitted from the battery manager 242 is output on the display 235, and control the operation of the sound outputter 244 so that the SOC information of the battery is output on the sound outputter 244.

The processor 250 may be configured to receive the SOC information about the SOC of the battery from the battery manager 242, determine whether charging of the battery 201 is required based on the SOC information, and, upon determining that charging of the battery 201 is required, control the display 235 to output information indicating a need to charge the battery 201. Here, the SOC information of the battery may include the charge amount of the battery.

The processor 250 may be configured to, upon receiving a charging command of the battery through the inputter 230, control the display 235 to display SOC information about the current SOC of the battery.

The configuration of control of the processor 250 may be the same as that of the processor 150 according to the above described embodiment.

Additionally, the processor 250 may be configured to, upon determining that the acquired strength of the magnetic field is greater than or equal to the reference strength, check the SOC of the battery, and, upon determining that the checked SOC is greater than or equal to a reference SOC, control stop the regenerative braking, and, upon determining that the checked SOC is less than the reference SOC, maintain regenerative braking.

Here, the reference SOC may be a SOC of 10%.

The memory 251 may be configured to store information about the reference SOC.

The resistive wire controller 123 and the processor 250 may be implemented as one processor.

At least one component may be added or omitted to correspond to the performance of the components of the vehicle shown in FIG. 7. In addition, the mutual positions of the components may be changed to correspond to the performance or structure of the system.

The components shown in FIG. 7 may refer to a software component and/or a hardware component, such as a Field Programmable Gate Array (FPGA) and an Application Specific Integrated Circuit (ASIC).

Figure 8:
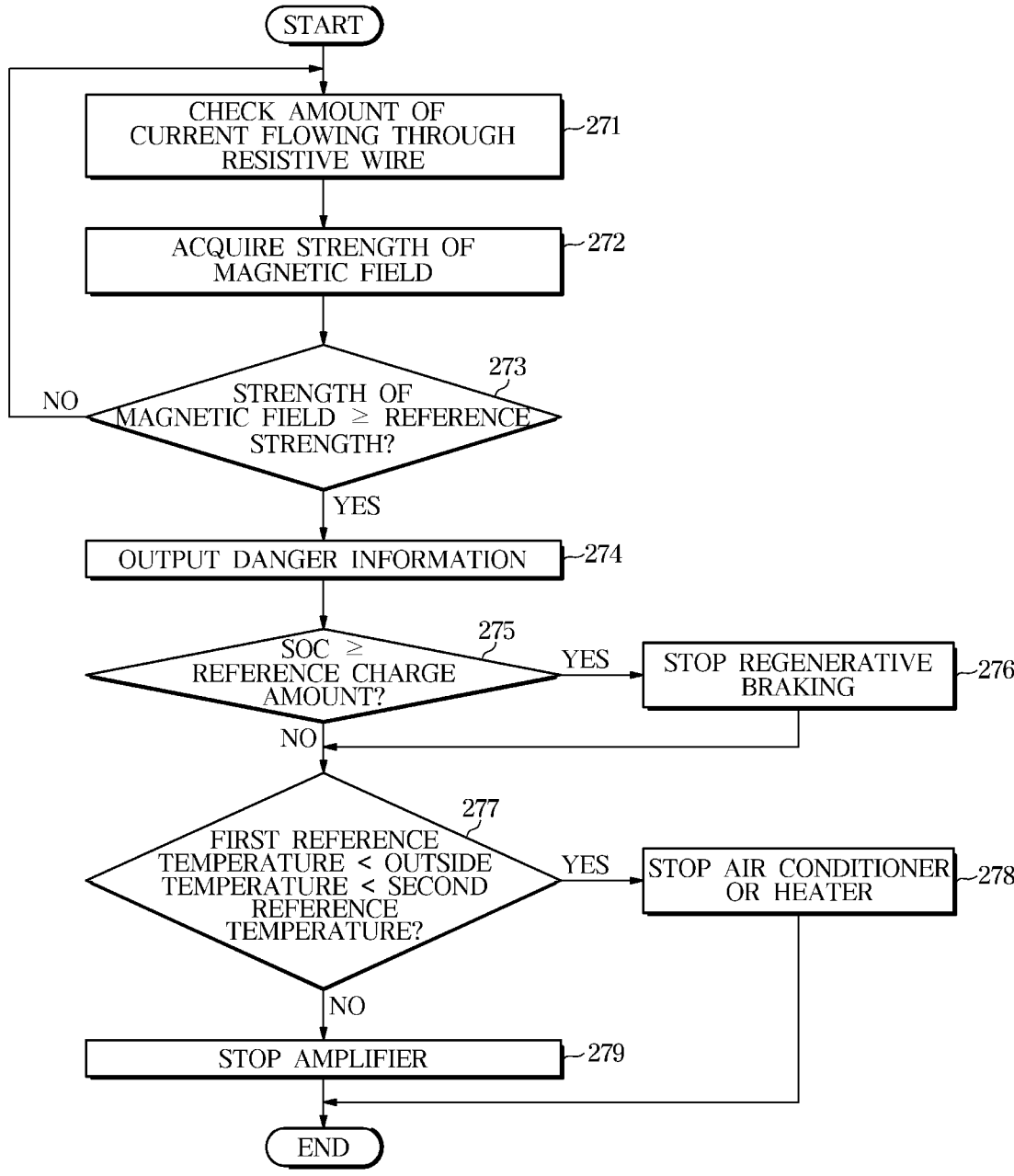
FIG. 8 is a control flowchart of a vehicle according to another exemplary embodiment.

FIG. 8 is a control flowchart of a vehicle according to another exemplary embodiment.

The vehicle may be configured to detect the amount of current flowing through the resistive wire of the steering wheel using the current sensor 127 provided on the steering wheel 120, and may be configured to check the amount of current detected through the current sensor 127 (271) (see FIG. 2).

The amount of current flowing through the resistive wire 121 of the steering wheel, when the resistive wire 121 is in an on state, may be a summation of the amount of the target current for operating the resistive wire 121 and the amount of current induced in the resistive wire 121.

The amount of current flowing through the resistive wire 121, when the resistive wire 121 is in an off state, may be a total amount of currents induced in the resistive wire 121.

The vehicle may be configured to check radius information of the steering wheel, position information of the steering wheel, position information of the seat, and angle information of the seat back of the seat, and acquires a distance d' between the center position of the steering wheel and the center position of the seat based on the checked position information of the steering wheel, the checked position information of the seat, and the checked angle information of the seat back.

Then, the vehicle may be configured to acquire a distance d from the center position of the steering wheel to the upper body of the driver based on the acquired distance, d', and the average chest thickness of adults.

In this case, the vehicle may be configured to acquire the distance, d, from the center position of the steering wheel to the upper body of the driver by subtracting a half of the average chest thickness of adults from the distance d' between the center position of the steering wheel and the center position of the seat $(d = d' - 01 \cdot m)$ Then, the vehicle may be configured to acquire the strength of a magnetic field generated by the circular resistive wire 121 having a radius 'a', at a point corresponding to the distance, d, from the center position of the steering wheel to the center position of the driver's upper body under the conditions of the radius 'a' of the resistive wire 121 and the distance, d, from the center position of the steering wheel to the center position of the driver's upper body.

In more detail, the vehicle may be configured to acquire the strength of the magnetic field, Bx, generated in the vicinity of the center of the steering wheel 120.

The vehicle may be configured to control the display 235 or the cluster 213 to display the strength of the magnetic field generated in the vicinity of the center of the steering wheel 120 or the upper body of the driver, so that the driver may identify the strength of the magnetic field that reaches the driver in real time.

The vehicle may be configured to determine whether the acquired strength of the magnetic field is greater than or equal to the reference strength (273), and, upon determining that the acquired strength of the magnetic field is greater than or equal to the reference strength, output notification information about a danger (274).

The vehicle may be configured to display the notification information of a danger as an image through the display 135 and the cluster 113, or may be configured to output the notification information of a danger as a sound through the sound outputter.

The vehicle may be configured to receive SOC information about a SOC of the battery 201, and determine whether the SOC of the battery 201 is greater than or equal to the reference SOC based on the received SOC information (S275), and, upon determining that the SOC of the battery 201 is greater than or equal to the reference SOC, stop regenerative braking.

The determining of whether the SOC of the battery 201 is greater than or equal to the reference SOC may include determining whether the charge amount of the battery is greater than or equal to a reference charge amount.

The vehicle may be configured to, upon determining that the SOC of the battery 201 is less than or equal to the reference SOC, check the outdoor temperature acquired through the outdoor temperature sensor, and determine whether the outdoor temperature is higher than the first reference temperature and lower than the second reference temperature (277), and, upon determining that that the outdoor temperature is higher than the first reference temperature and lower than the second reference temperature, check an electric device in operation among the air conditioner, the seat heating element, and the heater, and, upon checking that two or more electric devices are in operation, stop at least one of the two or more electric devices (278).

The vehicle may be configured to, upon determining that the outdoor temperature is lower than or equal to the first reference temperature or is higher than or equal to the second reference temperature, change an operation level of at least one of the air conditioner, the seat heating element, or the heater.

The vehicle may be configured to, upon determining that the SOC of the battery 201 is less than the reference SOC, check the outdoor temperature detected by the outdoor temperature sensor, and, upon determining that the outdoor temperature is lower than or equal to the first reference temperature or is higher than or equal to the second reference temperature, check a plurality of electric devices operating in the vehicle, identify an electric device having the largest amount of current among the checked electric devices, and stop the operation of the electric device having the largest amount of current.

For example, the vehicle may be configured to, upon determining that the electric device having the largest amount of current among the plurality of electric devices operating in the vehicle is an amplifier of the sound outputter, stop the operation of the amplifier (279).

Here, the first reference temperature may be a temperature lower than the second reference temperature. For example, the first reference temperature may be 0° C., and the second reference temperature may be 30° C.

The vehicle may also be configured to check the outdoor temperature transmitted from a server (not shown) through the communicator.

Meanwhile, the disclosed embodiments may be embodied in the form of a recording medium storing instructions executable by a computer. The instructions may be stored in the form of program code and, when executed by a processor, may be configured to generate a program module to perform the operations of the disclosed embodiments. The recording medium may be embodied as a computer-readable recording medium.

The computer-readable recording medium may include all kinds of recording media in which instructions which may be decoded by a computer are stored, for example, a Read Only Memory (ROM), a Random-Access Memory (RAM), a magnetic tape, a magnetic disk, a flash memory, an optical data storage device, and the like.

As is apparent from the above, the vehicle according to the present disclosure may be configured to monitor the strength of the magnetic field directed to the upper body of the driver in real time even during a travel, and, upon determining that the strength of the magnetic field has reached a level dangerous to the driver's health according to a result of the monitoring, output a notification about a danger so that the driver can escape from a dangerous situation. In other words, the health of the driver can be secured. In particular, the present disclosure can secure the safety of a driver into whom a cardiac pacemaker among active implantable medical devices is implanted.

The vehicle according to the present disclosure may be configured to control the operation of at least one electric device provided in the vehicle upon determination that the strength of the magnetic field reaches a level dangerous to the driver's health, so that the strength of the magnetic field generated inside the vehicle may be reduced. Accordingly, the strength of the magnetic field generated inside the vehicle may be reduced without obstructing the traveling.

The vehicle according to the present disclosure may be configured to monitor the strength of the magnetic field directed to the upper body of the user, in real-time, without installation of additional hardware. That is, an increase in the cost of the vehicle may be prevented.

As described above, the vehicle according to the present disclosure can improve the quality and marketability of the vehicle, further increase user satisfaction, improve vehicle safety, and secure product competitiveness.

Although embodiments of the present disclosure have been described for illustrative purposes, those skilled in the art will appreciate that various modifications, additions and substitutions are possible, without departing from the scope and spirit of the disclosure. Therefore, embodiments of the present disclosure have not been described for limiting purposes.

What is claimed is:

1. A vehicle comprising:
   a display;
   a resistive wire provided on a steering wheel;
   a current sensor configured to detect an amount of current flowing through the resistive wire;
   a plurality of electric devices; and
   a processor configured to:
      acquire a strength of a magnetic field generated inside the vehicle on a basis of radius information of the steering wheel, position information of the steering wheel, position information of a seat, angle information of a seat back of the seat, and the amount of current detected by the current sensor; and
      control the display to display notification information about a danger on a basis of the strength of the magnetic field and a reference strength;
   wherein, when the strength of the magnetic field is greater than or equal to the reference strength, the processor is further configured to:
      check a priority order of the plurality of electric devices or amounts of current of the plurality of electric devices; and
      control an operation of an electric device of the plurality of electric devices on a basis of the priority or the amounts of current.

2. The vehicle of claim 1, wherein the display is provided on at least one of a cluster or a terminal.

3. The vehicle of claim 1, wherein the reference strength comprises a magnetic field strength corresponding to a standard magnetic field strength of an active implantable medical device.

4. The vehicle of claim 1, wherein, in the controlling of the operation of an electric device, the processor is further configured to:
   check a priority order of the plurality of electric devices;
   identify an electric device, of the plurality of electric devices, having a highest priority; and
   stop an operation of the identified electric device.

5. The vehicle of claim 1, wherein, in the controlling of the operation of an electric device, the processor is further configured to:

check a priority order of the plurality of electric devices;

identify an electric device, of the plurality of electric devices, having a highest priority; and change an operation level of the identified electric device.

6. The vehicle of claim 1, wherein, in the controlling of the operation of an electric device, the processor is further configured to:

check amounts of current of the plurality of electric devices;

identify an electric device, of the plurality of electric devices, having a largest amount of current on a basis of the amounts of current of the plurality of electric devices; and stop an operation of the identified electric device.

7. The vehicle of claim 1, wherein, in the controlling of the operation of the electric device, the processor is further configured to:

check amounts of current of the plurality of electric devices;

identify an electric device of the plurality of electric devices having a largest amount of current on a basis of the amounts of current of the plurality of electric devices priority; and change an operation level of the identified electric device.

8. The vehicle of claim 1, wherein the processor is further configured to:

check the radius information of the steering wheel, the position information of the steering wheel, the position information of the seat, and the angle information of the seat back of the seat.

9. The vehicle of claim 1, wherein, when an outside temperature is higher than a first reference temperature and lower than a second reference temperature, the processor is further configured to stop an operation of at least one of a conditioner, a resistive wire of a seat, and a heater.

10. The vehicle of claim 9, wherein, when the outside temperature is lower than or equal to the first reference temperature or higher than or equal to the second reference temperature, the processor is further configured to stop an operation of an amplifier of a sound outputter.

11. A vehicle comprising:

a battery;

a driving motor configured to:

generate a driving force using electric power charged in the battery;

perform regenerative braking; and allow the battery to be charged through the regenerative braking;

a display;

a resistive wire provided on a steering wheel;

a current sensor configured to detect an amount of current flowing through the resistive wire;

a plurality of electric devices; and a processor configured to:

acquire a strength of a magnetic field generated inside the vehicle on a basis of radius information of the steering wheel, position information of the steering wheel, position information of a seat, angle information of a seat back of the seat, and the amount of current detected by the current sensor;

control the display to display notification information about a danger on a basis of the strength of the magnetic field and a reference strength; and control regenerative braking of the driving motor;

wherein, when the strength of the magnetic field is greater than or equal to the reference strength, the processor is further configured to:

check a priority order of the plurality of electric devices or amounts of current of the plurality of electric devices; and control an operation of an electric device of the plurality of electric devices on a basis of the priority or the amounts of current.

12. The vehicle of claim 11, wherein:

when the strength of the magnetic field is greater than or equal to the reference strength, the processor is further configured to check a charge amount of the battery, and when the charge amount checked is greater than or equal to a reference charge amount, the processor is further configured to stop the regenerative braking.

13. The vehicle of claim 11, wherein the reference strength includes a magnetic field strength corresponding to a standard magnetic field strength of an active implantable medical device.

14. The vehicle of claim 11, wherein, in controlling of the operation of an electric device, the processor is further configured to:

check a priority order of the plurality of electric devices;

identify an electric device of the plurality of electric devices having a highest priority; and stop an operation of the identified electric device or change an operation level of the identified electric device.

15. The vehicle of claim 11, wherein, in controlling of the operation of an electric device, the processor is further configured to:

check amounts of current of the plurality of electric devices;

identify an electric device of the plurality of electric devices having a largest amount of current on a basis of the amounts of current of the plurality of electric devices; and stop an operation of the identified electric device or change an operation level of the electric device.

16. The vehicle of claim 11, wherein the processor is further configured to:

check the radius information of the steering wheel, the position information of the steering wheel, the position information of the seat, and the angle information of the seat back of the seat.

17. The vehicle of claim 11, wherein, when an outside temperature is higher than a first reference temperature and lower than a second reference temperature, the processor is further configured to stop an operation of at least one of a conditioner, a resistive wire of a seat, or a heater.

18. The vehicle of claim 17, wherein, when the outside temperature is lower than or equal to the first reference temperature or higher than or equal to the second reference temperature, the processor is further configured to stop an operation of an amplifier of a sound outputter.

19. The vehicle of claim 11, wherein, when the strength of the magnetic field is greater than or equal to the reference strength, the processor is further configured to control the display to display the notification information.

20. The vehicle of claim 11, wherein, when the resistive wire is in an off state, the current sensor is further configured to detect an amount of current induced on the resistive wire.

* * * * *